(12) United States Patent
Li et al.

(10) Patent No.: US 12,211,257 B2
(45) Date of Patent: Jan. 28, 2025

(54) IMAGE PROCESSING METHOD, APPARATUS, AND SYSTEM

(71) Applicant: Huawei Cloud Computing Technologies Co., Ltd., Gui'an New District (CN)

(72) Inventors: Yaoxin Li, Shenzhen (CN); Changzheng Zhang, Shenzhen (CN); Xiaoshi Chen, Shenzhen (CN); Dandan Tu, Shenzhen (CN)

(73) Assignee: HUAWEI CLOUD COMPUTING TECHNOLOGIES CO., LTD., Guiyang (CN)

( * ) Notice: Subject to any disclaimer, the term of this patent is extended or adjusted under 35 U.S.C. 154(b) by 417 days.

(21) Appl. No.: 17/590,005

(22) Filed: Feb. 1, 2022

(65) Prior Publication Data

US 2022/0156931 A1 May 19, 2022

Related U.S. Application Data

(63) Continuation of application No. PCT/CN2019/121731, filed on Nov. 28, 2019.

(51) Int. Cl.
*G06V 10/80* (2022.01)
*G06T 7/00* (2017.01)
(Continued)

(52) U.S. Cl.
CPC .......... *G06V 10/809* (2022.01); *G06T 7/0012* (2013.01); *G06T 7/11* (2017.01);
(Continued)

(58) Field of Classification Search
CPC ...... G06V 10/809; G06V 10/82; G06V 10/50; G06V 10/774; G06V 10/746;
(Continued)

(56) References Cited

U.S. PATENT DOCUMENTS

2015/0297949 A1* 10/2015 Aman ..................... G06T 7/246
348/157
2021/0058595 A1* 2/2021 Zhang ................... G06T 3/4015

FOREIGN PATENT DOCUMENTS

CN 102682305 A 9/2012
CN 105259095 A 1/2016
(Continued)

OTHER PUBLICATIONS

International Search Report and Written Opinion issued in PCT/CN2019/121731, dated Aug. 26, 2020, 11 pages.
(Continued)

*Primary Examiner* — John J Lee

(57) ABSTRACT

This application relates to the artificial intelligence field, and provides an image processing method, an apparatus, and a system. The image processing method includes: obtaining a plurality of image blocks by segmenting a to-be-analyzed pathological image; inputting the plurality of image blocks to a first analysis model to obtain a first analysis result, where the first analysis model classifies each of the plurality of image blocks based on a quantity or an area of suspicious lesion components; inputting at least one second-type image block in the first analysis result to a second analysis model to obtain a second analysis result, where the second analysis model analyzes a location of a suspicious lesion component of each input second-type image block; and obtaining a final analysis result of the pathological image based on the first analysis result and the second analysis result.

20 Claims, 7 Drawing Sheets

(51) Int. Cl.
- *G06T 7/11* (2017.01)
- *G06T 7/70* (2017.01)
- *G06V 10/50* (2022.01)
- *G06V 10/764* (2022.01)
- *G06V 10/774* (2022.01)
- *G06V 10/82* (2022.01)
- *G16H 30/40* (2018.01)
- *G16H 50/20* (2018.01)

(52) U.S. Cl.
CPC ............... *G06T 7/70* (2017.01); *G06V 10/50* (2022.01); *G06V 10/764* (2022.01); *G06V 10/774* (2022.01); *G06V 10/82* (2022.01); *G16H 30/40* (2018.01); *G16H 50/20* (2018.01); *G06T 2207/20021* (2013.01); *G06T 2207/20081* (2013.01); *G06T 2207/20084* (2013.01); *G06T 2207/30024* (2013.01); *G06T 2207/30096* (2013.01); *G06T 2207/30168* (2013.01); *G06V 2201/03* (2022.01)

(58) Field of Classification Search
CPC ......... G06V 2201/03; G06T 7/11; G06T 7/70; G06T 7/0012; G06T 2207/20021; G06T 2207/20081; G06T 2207/20084; G06T 2207/30024; G06T 2207/30096; G06T 2207/30168; G16H 50/20; G16H 30/40
See application file for complete search history.

(56) References Cited

FOREIGN PATENT DOCUMENTS

| | | | | |
|---|---|---|---|---|
| CN | 106127255 A | 11/2016 | | |
| CN | 106991673 A | 7/2017 | | |
| CN | 108596882 A | 9/2018 | | |
| CN | 108629772 A | * 10/2018 | ........... | G06T 7/0012 |
| CN | 108765408 A | 11/2018 | | |
| CN | 109493308 A | 3/2019 | | |
| CN | 109583440 A | 4/2019 | | |
| CN | 110007455 A | 7/2019 | | |
| CN | 110110750 A | 8/2019 | | |
| CN | 110121749 A | 8/2019 | | |
| WO | 2019005722 A1 | 1/2019 | | |

OTHER PUBLICATIONS

Extended European Search Report issued in EP 19954469, dated Jun. 23, 2022, 8 pages.

* cited by examiner

IMAGE PROCESSING METHOD, APPARATUS, AND SYSTEM

CROSS-REFERENCE TO RELATED APPLICATIONS

This application is a continuation of International Application No. PCT/CN2019/121731, filed on Nov. 28, 2019, the disclosure of which is hereby incorporated by reference in its entirety.

TECHNICAL FIELD

This application relates to the artificial intelligence (AI) field, and more specifically, to a method, an apparatus, and a system for image processing.

BACKGROUND

With rapid development of image digitization and digital storage technologies, currently, a pathological slide is usually scanned into a digital pathological image, so that a doctor can directly read the pathological image on a computer without using a microscope. However, even an experienced doctor may misdiagnose when performing diagnosis based on a large quantity of digital pathological images. Therefore, how to better process the digital pathological image to provide a more accurate analysis or diagnosis result based on the pathological image becomes an urgent problem to be resolved.

SUMMARY

Embodiments of this application provide an image processing method, an apparatus, and a system, to determine a pathological image, reduce determination errors caused by a human subjective factor, help a doctor with little or no related experience obtains an analysis result of the pathological image, and help the doctor to diagnose a patient's condition.

According to a first aspect, an embodiment of this application provides a pathological image processing method, including: obtaining a plurality of image blocks, where the plurality of image blocks are obtained by segmenting a to-be-analyzed pathological image; inputting the plurality of image blocks to a first analysis model to obtain a first analysis result, where the first analysis model classifies each of the plurality of image blocks based on a quantity or an area of suspicious lesion components, the first analysis result indicates that a type of each image block is a first type or a second type, the first type indicates that a quantity or an area of suspicious lesion components in the image block is greater than or equal to a preset threshold, and the second type indicates that the quantity or the area of the suspicious lesion components in the image block is less than the preset threshold; inputting at least one second-type image block in the first analysis result to a second analysis model to obtain a second analysis result, where the second analysis model analyzes a location of a suspicious lesion component of each input second-type image block; and obtaining a final analysis result of the pathological image based on the first analysis result and the second analysis result. The first analysis model may also be referred to as an image block classification model. The second analysis model may also be referred to as a suspicious lesion component detection model. An image block whose type is the first type may also be referred to as a first-type image block. An image block whose type is the second type may also be referred to as a second-type image block.

In the technical solution, the pathological image may be processed by using the first analysis model and the second analysis model, to obtain the analysis result of the pathological image. Therefore, determination errors caused by a human subjective factor can be reduced. In addition, interpretation of the pathological image is less dependent on an experienced doctor. A doctor with little or no related experience can obtain the analysis result of the pathological image. This helps the doctor to diagnose a patient's condition.

With reference to the first aspect, in a possible implementation of the first aspect, the method further includes: inputting each image block to a third analysis model to obtain a third analysis result, where the third analysis model predicts image quality of each image block. The obtaining a final analysis result of the pathological image based on the first analysis result and the second analysis result includes: obtaining the final analysis result of the pathological image based on the first analysis result, the second analysis result, and the third analysis result. Quality information of the pathological image may be used to assist in determining the analysis result of the pathological image.

The third analysis model may also be referred to as an image quality prediction model.

With reference to the first aspect, in a possible implementation of the first aspect, the obtaining a plurality of image blocks includes: obtaining a plurality of initial image blocks formed after the to-be-analyzed pathological image is segmented; and inputting each of the plurality of initial image blocks to a style transfer model to obtain the plurality of image blocks, where the style transfer model converts a style of each initial image block. Styles of the image blocks are unified through style transfer, to improve accuracy of a classification result of the image blocks and a detection result of the suspicious lesion component, so as to improve the analysis result of the pathological image.

With reference to the first aspect, in a possible implementation of the first aspect, the method further includes: training an initial first analysis model based on a first training data set to obtain the first analysis model. The initial first analysis model is one of artificial intelligence AI models. The first training data set includes a plurality of first training images, and a label of each first training image is a first type or a second type. The first training data set is also referred to as a training data set 2.

The first analysis model may also be referred to as the image block classification model. The image block classification model may be obtained by training a training image that is marked by a plurality of experienced doctors or pathologists. Therefore, the accuracy of the result of classifying the image blocks by using the image block classification model is high.

With reference to the first aspect, in a possible implementation of the first aspect, the method further includes: training an initial second analysis model based on a second training data set to obtain the second analysis model, where the initial second analysis model is one of the artificial intelligence (AI) models, the second training data set includes a plurality of second training images including a suspicious lesion component, and a label of each second training image is location information of the suspicious lesion component in the training image. The second training data set is also referred to as a training data set 3.

The second analysis model may also be referred to as the suspicious lesion component detection model. The suspicious lesion component detection model may be obtained by training a training image that is marked by a plurality of experienced doctors or pathologists. Therefore, the accuracy of the detection result of detecting the suspicious lesion component in the image block by using the suspicious lesion component detection model is high.

With reference to the first aspect, in a possible implementation of the first aspect, the method further includes: training an initial third analysis model based on a third training data set to obtain the third analysis model, where the initial third analysis model is one of the artificial intelligence AI models, the third training data set includes a plurality of third training images, and a label of each third training image is an image quality type of each third training image. The third training data set is also referred to as a training data set 1.

With reference to the first aspect, in a possible implementation of the first aspect, the obtaining a final analysis result of the pathological image based on the first analysis result and the second analysis result includes: inputting the first analysis result and the second analysis result to a decision model to obtain the final analysis result of the pathological image.

With reference to the first aspect, in a possible implementation of the first aspect, the pathological image is a pathological image of a cervical cell, and the suspicious lesion component is a positive cervical cell.

According to a second aspect, an embodiment of this application provides a data processing apparatus, including: an obtaining unit, configured to obtain a plurality of image blocks, where the plurality of image blocks are obtained by segmenting a to-be-analyzed pathological image; an image analysis unit, configured to input the plurality of image blocks to a first analysis model to obtain a first analysis result, where the first analysis model classifies each of the plurality of image blocks based on a quantity or an area of suspicious lesion components, the first analysis result indicates that a type of each image block is a first type or a second type, the first type indicates that a quantity or an area of suspicious lesion components in the image block is greater than or equal to a preset threshold, the second type indicates that the quantity or the area of the suspicious lesion components in the image block is less than the preset threshold, the image analysis unit is further configured to input at least one second-type image block in the first analysis result to a second analysis model to obtain a second analysis result, and the second analysis model analyzes a location of a suspicious lesion component of each input second-type image block; and a decision analysis unit, configured to obtain a final analysis result of the pathological image based on the first analysis result and the second analysis result.

With reference to the second aspect, in a possible implementation of the second aspect, the apparatus further includes an image quality detection unit, configured to input each image block to a third analysis model to obtain a third analysis result. The third analysis model predicts image quality of each image block. The decision analysis unit is further configured to obtain the final analysis result of the pathological image based on the first analysis result, the second analysis result, and the third analysis result.

With reference to the second aspect, in a possible implementation of the second aspect, the obtaining unit is further configured to obtain a plurality of initial image blocks formed after the to-be-analyzed pathological image is segmented, and input each of the plurality of initial image blocks to a style transfer model to obtain the plurality of image blocks. The style transfer model converts a style of each initial image block.

With reference to the second aspect, in a possible implementation of the second aspect, the apparatus further includes a first training unit, configured to train an initial first analysis model based on a first training data set to obtain the first analysis model. The initial first analysis model is one of artificial intelligence AI models. The first training data set includes a plurality of first training images, and a label of each first training image is a first type or a second type.

With reference to the second aspect, in a possible implementation of the second aspect, the apparatus further includes a second training unit, configured to train an initial second analysis model based on the second training data set to obtain the second analysis model. The initial second analysis model is one of the artificial intelligence AI models. The second training data set includes a plurality of second training images including a suspicious lesion component, and a label of each second training image is location information of the suspicious lesion component in the training image.

With reference to the second aspect, in a possible implementation of the second aspect, the apparatus further includes a third training unit, configured to train an initial third analysis model based on the third training data set to obtain the third analysis model. The initial third analysis model is one of the artificial intelligence AI models. The third training data set includes a plurality of third training images, and a label of each third training image is an image quality type of each third training image.

With reference to the second aspect, in a possible implementation of the second aspect, the decision analysis unit is further configured to input the first analysis result and the second analysis result to a decision model to obtain the final analysis result of the pathological image.

According to a third aspect, this application provides a computing device system, including at least one memory and at least one processor. The at least one memory is configured to store a computer instruction. When the at least one processor executes the computer instruction, the computing device system performs the method provided in any one of the first aspect or the possible implementations of the first aspect.

According to a fourth aspect, this application provides a non-transitory computer readable storage medium storing instructions that, when executed by a computing device, cause the computing device to perform the method provided in any one of the first aspect or the possible implementations of the first aspect. The storage medium includes but is not limited to a volatile memory, for example, a random access memory or a non-volatile memory, for example, a flash memory, a hard disk drive (HDD), or a solid-state drive (SSD).

According to a fifth aspect, this application provides a computer program product. The computer program product includes computer instructions. When the computer instructions are executed by a computing device, the computing device performs the method provided in any one of the first aspect or the possible implementations of the first aspect. The computer program product may be a software installation package. When the method provided in any one of the first aspect or the possible implementations of the first aspect is used, the computer program product may be downloaded to and executed on the computing device.

DESCRIPTION OF EMBODIMENTS

Figure 1:
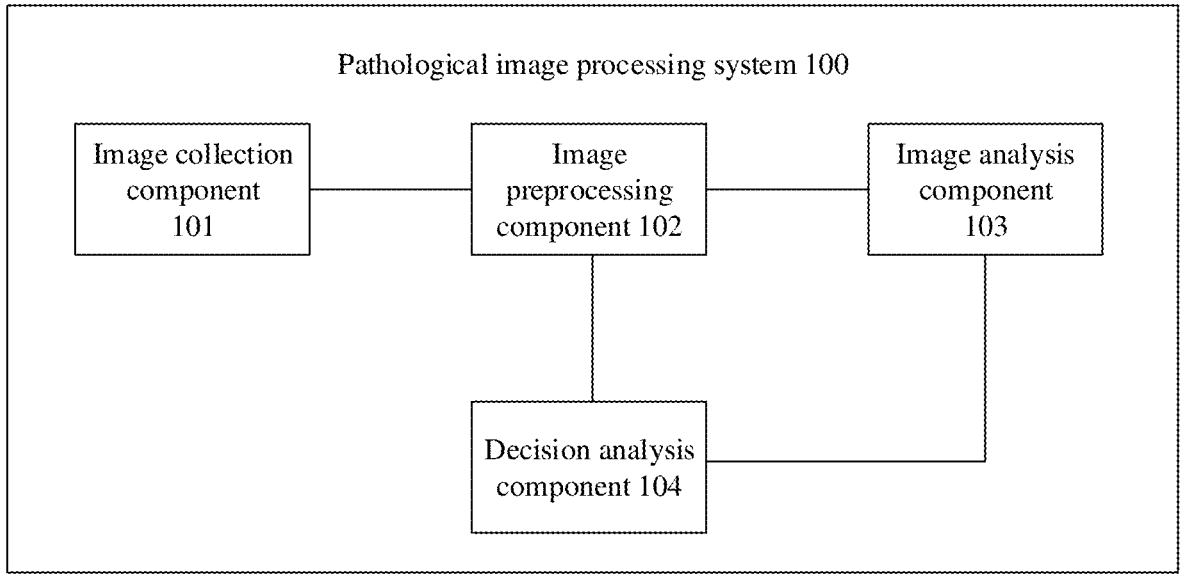
FIG. 1 is a schematic structural block diagram of a pathological image processing system according to an embodiment of this application.

The following describes the technical solutions of this application with reference to the accompanying drawings.

All aspects, embodiments, or features are presented in this application by describing a system that may include a plurality of devices, components, modules, and the like. It should be appreciated and understood that, each system may include another device, component, module, and the like, and/or may not include all devices, components, modules, and the like discussed with reference to the accompanying drawings. In addition, a combination of the solutions may be used.

In addition, in embodiments of this application, the terms such as "for example", "such as" are used to represent giving an example, an illustration, or a description. Any embodiment or design solution described as an "example" in this application should not be explained as being more preferred or having more advantages than another embodiment or design solution. Exactly, "for example" is used to present a concept in a specific manner.

A network architecture and a service scenario described in the embodiments of this application are intended to describe the technical solutions in the embodiments of this application more clearly, and do not constitute a limitation on the technical solutions provided in the embodiments of this application. A person of ordinary skill in the art may know that: With evolution of the network architecture and emergence of a new service scenario, the technical solutions provided in the embodiments of this application are also applicable to similar technical problems.

Reference to "an embodiment", "some embodiments", or the like described in this specification indicates that one or more embodiments of this application include a specific feature, structure, or characteristic described with reference to the embodiments. Therefore, in this specification, statements, such as "in an embodiment", "in some embodiments", "in some other embodiments", and "in other embodiments", that appear at different places do not necessarily mean referring to a same embodiment, instead, they mean "one or more but not all of the embodiments", unless otherwise specifically emphasized. The terms "include", "comprise", "have", and their variants all mean "include but are not limited to", unless otherwise specifically emphasized.

In this application, "at least one" means one or more, and "a plurality of" means two or more. The term "and/or" describes an association relationship between associated objects and may indicate three relationships. For example, A and/or B may indicate the following cases: Only A exists, both A and B exist, and only B exists, where A and B may be singular or plural. The character "/" usually indicates an "or" relationship between the associated objects. "At least one (piece) of the following" or a similar expression thereof indicates any combination of these items, including any combination of singular items (pieces) or plural items (pieces). For example, at least one (piece) of a, b, or c may represent: a, b, c, a-b, a-c, b-c, or a-b-c, where a, b, and c may be singular or plural.

Pathological examination is a pathological morphological examination method used to examine a pathological change in organs, tissues or cells. The pathological examination can provide a basis for a doctor to diagnose a disease.

Morphological examination is one of common pathological examination methods. The morphological examination can be classified into exfoliative cytologic examination and biopsy. In the exfoliative cytologic examination, an exfoliative cell in human organs is collected, and after the collected cells are stained, the pathological examination is performed by observing these stained cells. Common exfoliative cytologic examinations include a sputum smear test for a lung cancer, a urine centrifugal smear test for a urological cancer, and the like. In the biopsy, a pathological slide is made from a small piece of tissue removed from a lesion component of a patient's body, and the pathological examination is performed by observing a morphological structural change of a cell and/or a tissue in the pathological slide.

Objects of the pathological examination may include any component that can be used for the pathological examination, for example, a cell, cell debris, a nucleus, an intracellular substance (for example, alveolar macrophage hemosiderosis, deposition of an intracellular substance), another tissue or substance (for example, a fibrous protein and a protein-like substance) that can be observed by using a microscope. For ease of description, in the embodiments of this application, the object of the pathological examination is referred to as a component.

It should be understood that, for different pathological examinations, the objects of the pathological examinations, namely, components, are different. For example, in a pathological examination for a cervical cancer, a cervical cell is usually used as a component, and pathological detection is performed on a pathological slide made from the cervical cell. Optionally, from a perspective of division into results, components in the pathological examination may be classified into two types. One type is a normal component, and the other type is a component different from the normal component (for example, a lesion component, a suspicious lesion component). Cells are used as an example. One type is a normal cell, and the other type is an abnormal cell, for example, may be a cell in which a lesion or a suspicious lesion cell occurs, for another example, may be cell debris, or for another example, may be a cell including a specific substance (for example, hemosiderosis or a deposited substance).

The pathological slide described in the embodiments of this application is a pathological specimen made from a component such as an exfoliative cell or a living tissue. For some pathological examination, a to-be-examined component needs to be smeared on the slide. Therefore, the formed pathological slide may also be referred to as a smear. A pathological image described in the embodiments of this application is an image obtained by performing digital processing (for example, scanning and photographing) on the pathological slide.

Currently, the pathological examination is usually performed by a professional doctor by using a microscope to observe the pathological slide or by using a computer to observe the pathological image, to provide an examination result of the pathological image. The examination result of the pathological image is usually used for disease diagnosis. On the one hand, a method relying only on the doctor to perform the pathological examination greatly increases a workload of the doctor. On the other hand, because some doctors may need to undertake a large quantity of pathological examination tasks, some doctors do not have a high professional skill, or the like, the examination result provided by the doctor may be incorrect.

As an artificial intelligence (AI) technology progresses, the AI technology is applied more deeply in the medical field. In embodiments of this application, the AI technology is applied to pathological image processing, and the examination result of a pathological image may be obtained based on the pathological image, to assist in medical diagnosis.

An embodiment of this application provides a pathological image processing system. The pathological image processing system may analyze a collected pathological image to obtain an output result. The output result is an examination result corresponding to the pathological image. A doctor can use the output result of the pathological image processing system to determine a patient's condition, perform auxiliary diagnosis, perform preoperative analysis, and the like.

For ease of description, in the following embodiments, it is assumed that a to-be-processed pathological image is a pathological image of a cervical cell, obtained by using a thinprep cytologic test (TCT) technology. Pathological examination on the pathological image of the cervical cell is usually used to preventively detect a cervical cancer and confirm a condition of a cervical cancer. Based on whether the cervical cell is normal or not, components (namely, the cervical cells) in the pathological image of the cervical cell can be classified into two types. One type is a suspicious lesion cell (usually referred to as a positive cell). The other type is a normal cell (usually referred to as a negative cell).

FIG. 1 is a schematic structural block diagram of a pathological image processing system according to an embodiment of this application. The pathological image processing system 100 shown in FIG. 1 includes an image collection component 101, an image preprocessing component 102, an image analysis component 103, and a decision analysis component 104.

The image collection component 101 is configured to obtain a pathological image, and segment the pathological image to obtain N image blocks, where N is a positive integer greater than or equal to 2.

A specific implementation of collecting the pathological image by the image collection component 101 is not limited in this embodiment of this application. For example, the image collection component 101 may scan a pathological slide to obtain the pathological image. For another example, the image collection component 101 may photograph a pathological slide to obtain the pathological image. For another example, the image collection component 101 may receive the pathological image from another device or apparatus.

A manner for segmenting the pathological image by the image collection component 101 is not limited in this embodiment of this application. Optionally, in some implementations, a value of N may be a preset fixed value or a manually set fixed value. For example, the fixed value may be 1000, 1500, 2000, or the like. Optionally, in some other implementations, a value of N may be related to a resolution of the pathological image. For example, if the resolution of the pathological image is less than 500×500, the value of N may be 500. If the resolution of the pathological image is greater than 500×500 and less than or equal to 1500×1500, the value of N may be 1000. If the resolution of the pathological image is greater than 1500×1500, the value of N may be 2000. Optionally, in some other implementations, a size of the image block may be a preset fixed value or a manually set fixed value. For example, a size of each image block may be 50×50. The value of N may be determined based on the size of the pathological image and the size of the preset image block or the manually set image block. Each image block may include at least a plurality of cells.

The image preprocessing component 102 may be configured to determine image quality of each of the N image blocks. The image preprocessing component 102 may further be configured to transfer a style of the image block, to obtain an image block after the style transfer.

The style transfer, also referred to as image style transfer, indicates fusing a style of a target image with a style of a reference image, so that a style of an output image obtained after the fusion is the same as or similar to the style of the reference image. The style of the image indicates a presentation of the image, for example, a color and a contrast. In the medical field, different pathological images may be obtained through scanning by different scanners, or different pathological slides are made from different dyeing materials. Therefore, the obtained pathological images may have different styles. By using a style transfer technology, a pathological image of a style can be converted into a pathological image having a same or similar style as the reference pathological image. A result obtained in subsequent image analysis on the pathological image after the style transfer is more accurate.

The image analysis component 103 may be configured to obtain the image block processed by the image preprocessing component 102, and classify the obtained image block based on a trained AI model, to determine a type of the obtained image block.

Optionally, in some embodiments, the image analysis component 103 may determine that the obtained image block is a first-type image block or a second-type image block. A quantity of suspicious lesion cells in the first-type image block is greater than or equal to a first preset threshold. A quantity of suspicious lesion cells in the second-type image block is less than the first preset threshold.

Optionally, in some other embodiments, the image analysis component 103 may determine that the obtained image block is a first-type image block, a second-type image block, or a third-type image block. A quantity of suspicious lesion cells in the first-type image block is greater than or equal to a first preset threshold. A quantity of suspicious lesion cells in the second-type image block is greater than or equal to a second preset threshold and is less than the first preset threshold. A quantity of suspicious lesion cells in the third-type image block is less than the second preset threshold.

The image analysis component 103 is further configured to detect the second-type image block obtained through classification, to detect a suspicious lesion cell in the second-type image block.

The decision analysis component 104 may be configured to obtain the first-type image block that is determined by the image analysis component 103 and a second-type image block that includes the suspicious lesion cell. The decision analysis component 104 may determine, based on the first-type image block and the second-type image block that includes the suspicious lesion cell, a target output result corresponding to the pathological image. Optionally, the decision analysis component 104 may further obtain image quality information output by the image preprocessing component 102. In this case, the decision analysis component may determine, based on the first-type image block, the second-type image block that includes the suspicious lesion cell, and the image quality information, the target output result corresponding to the pathological image.

Figure 2:
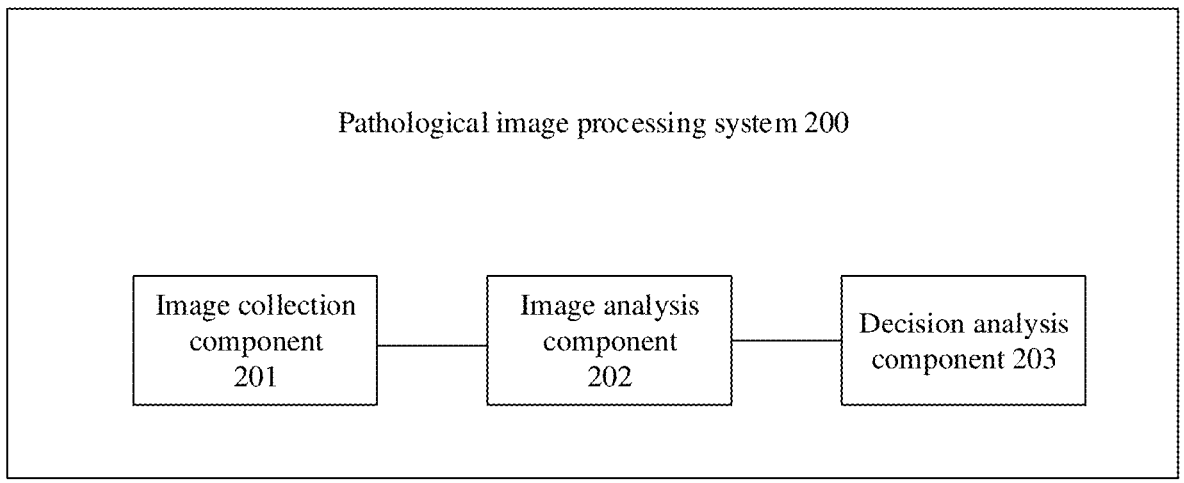
FIG. 2 is a schematic structural block diagram of another pathological image processing system according to an embodiment of this application.

Optionally, in another embodiment, a pathological image processing system 200 is further provided. As shown in FIG. 2, the pathological image processing system 200 includes an image collection component 201, an image analysis component 202, and a decision analysis component 203.

A function of the image collection component 201 is the same as a function of the image collection component 101. A function of the image analysis component 202 is the same as a function of the image analysis component 103. The decision analysis component 203 may be configured to obtain a first-type image block determined by the image analysis component 202 and a second-type image block including a suspicious lesion cell. The decision analysis component 203 may determine, based on the first-type image block and the second-type image block that includes the suspicious lesion cell, a target output result corresponding to a pathological image.

It should be understood that the division of components of the pathological image processing system is merely an example of division based on functions. A specific division manner of the internal components or modules of the pathological image processing system is not limited in embodiments of this application.

Figure 3:
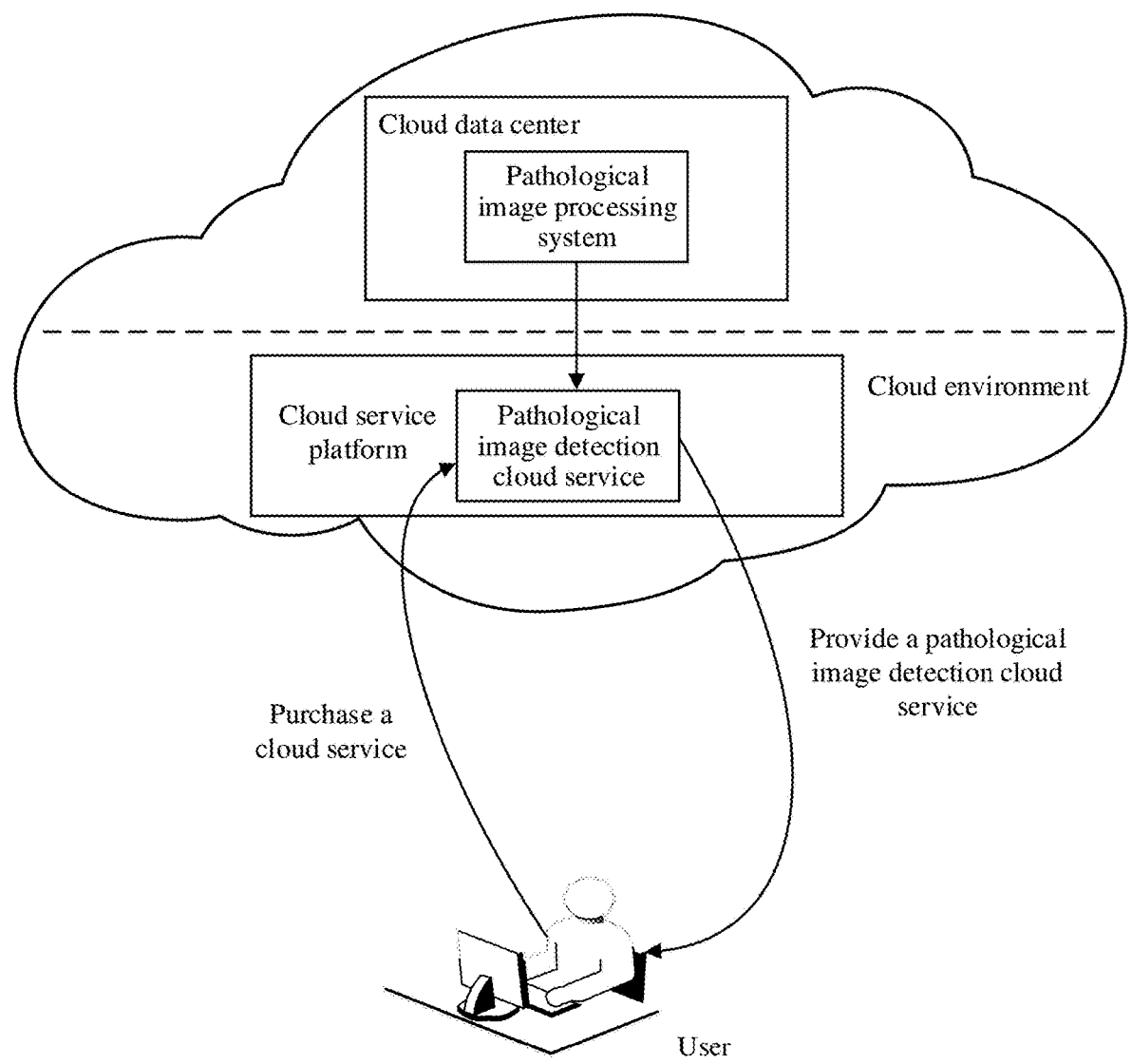
FIG. 3 is a schematic diagram of deployment of a pathological image processing system according to an embodiment of this application.

FIG. 3 is a schematic diagram of deployment of a pathological image processing system according to an embodiment of this application. All components of the pathological image processing system may be deployed in a cloud environment. The cloud environment is an entity providing a cloud service for a user in a cloud compute mode by using a basic resource. The cloud environment includes a cloud data center and a cloud service platform. The cloud data center includes a large quantity of basic resources (including a compute resource, a storage resource, and a network resource) owned by a cloud service provider. The compute resources included in the cloud data center may be a large quantity of computing devices (for example, servers). The pathological image processing system may be implemented by a server in the cloud data center. The pathological image processing system may alternatively be implemented by a virtual machine created in the cloud data center. The pathological image processing system may alternatively be a software apparatus independently deployed on the server or the virtual machine in the cloud data center. The software apparatus is configured to implement a function of the pathological image processing system. The software apparatus may alternatively be deployed on a plurality of servers in a distributed manner, or deployed on a plurality of virtual machines in a distributed manner, or deployed on the virtual machine and the server in a distributed manner.

As shown in FIG. 3, the pathological image processing system may be abstracted, by the cloud service provider on the cloud service platform, into a cloud service that is provided for the user. After the user purchases the cloud service on the cloud service platform, the cloud environment provides the user with the cloud service of pathological image detection by using the pathological image processing system. The user may upload a to-be-processed pathological image to the cloud environment through an application programming interface (API) or by using a web page provided by the cloud service platform. The pathological image processing system receives and detects the to-be-processed pathological image, and returns a detection result to a terminal of the user, or store a detection result in the cloud environment. For example, the detection result is displayed on the web page of the cloud service platform for the user to view.

When the pathological image processing system is the software apparatus, several parts of the pathological image processing system may be respectively deployed in different environments or on different devices. For example, a part of the pathological image processing system is deployed on a terminal computing device (for example, a terminal server, a smartphone, a notebook computer, a tablet computer, a personal desktop computer, or a smart camera), and another part is deployed in the data center (specifically deployed on the server or the virtual machine in the data center). The data center may be the cloud data center, or may be an edge data center. The edge data center is a set of edge computing devices deployed comparatively close to the terminal computing device.

All parts of the pathological image processing system deployed in the different environments or on the different devices collaboratively implement a pathological image processing function. For example, in a scenario, a scanning device is deployed with an image collection component of the pathological image processing system. The scanning device may scan a pathological slide to obtain a pathological image, segment the pathological image, and send a segmented image block to the data center through a network. The data center is deployed with an image preprocessing component, an image analysis component, and a decision analysis component. These components further process the segmented image block, and finally obtain an analysis result. The data center sends the analysis result to a computer, so that a doctor can obtain the analysis result of the pathological image. It should be understood that embodiments of this application do not limit which part of the pathological image processing system is deployed on the terminal computing device and which part is deployed in the data center. In an actual application, adaptive deployment may be performed based on a compute capability or a specific application requirement of the terminal computing device. For example, in another implementation, a scanning device may scan a pathological slide to obtain a pathological image, and upload the pathological image to the data center. The data center may perform segmentation processing and subsequent detection on the pathological image. It should be noted that, in an embodiment, the pathological image processing system may be further deployed in three parts. One part is deployed on the terminal computing device, one part is deployed in the edge data center, and one part is deployed in the cloud data center.

Figure 4:
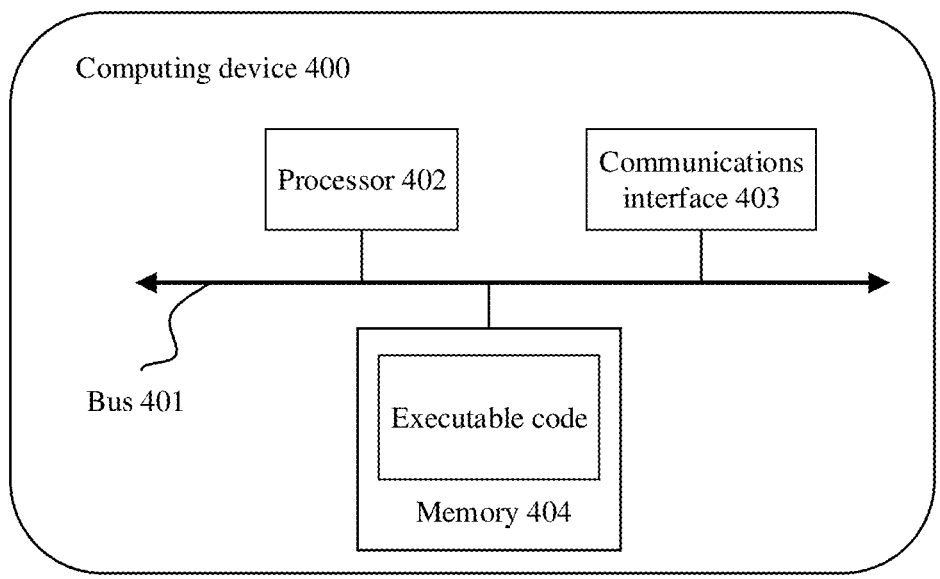
FIG. 4 is a schematic structural block diagram of a computing device according to an embodiment of this application.

When the pathological image processing system is the software apparatus, the pathological image processing system may alternatively be independently deployed on a computing device in any environment (for example, independently deployed on a terminal computing device or independently deployed on a computing device in the data center). As shown in FIG. 4, a computing device 400 includes a bus 401, a processor 402, a communications interface 403, and a memory 404. The processor 402, the memory 404, and the communications interface 403 communicate with each other through the bus 401. The processor 402 may be a central processing unit (CPU). The memory 404 may include a volatile memory, for example, a random access memory (RAM). The memory 404 may further include a non-volatile memory (NVM), for example, a read-only memory (ROM), a flash memory, an HDD, or an SSD. The memory 404 stores executable code included in a pathological image processing system. The processor 402 reads the executable code in the memory 404 to perform a pathological image processing method. The memory 404 may further include another software module, for example, an operating system, for running a process. The operating system may be Linux™, Unix™, Windows™, or the like.

In an embodiment of this application, a pre-trained AI model needs to be used to perform the pathological image processing method. The AI model is essentially an algorithm, and includes a large quantity of parameters and calculation formulas (or calculation rules). The AI model may be trained. The trained AI model can learn a rule and a feature in training data. In this embodiment of this application, a plurality of trained AI models having different functions may be used. For example, a trained AI model used to predict quality of an image block is referred to as an image quality prediction model. A trained AI model used to perform style transfer on an image block is referred to as a style transfer model. A trained AI model used to classify an image block is referred to as an image block classification model. A trained AI model used to detect a suspicious lesion component is referred to as a suspicious lesion component detection model. A trained AI model used to determine an analysis result of a pathological image is referred to as a decision model. The five models may be trained by a training system. The training system separately trains the image quality prediction model, the style transfer model, the image block classification model, the suspicious lesion component detection model, and the decision model by using different training sets. The image quality prediction model, the style transfer model, the image block classification model, the suspicious lesion component detection model, and the decision model that are trained by the training system are deployed in the pathological image processing system, and are used by the pathological image processing system to detect the pathological image.

It may be understood that, in some embodiments, the pathological image processing system may use only some of the five models. In this case, the training system may train only a model used by the pathological image processing system.

Figure 5:
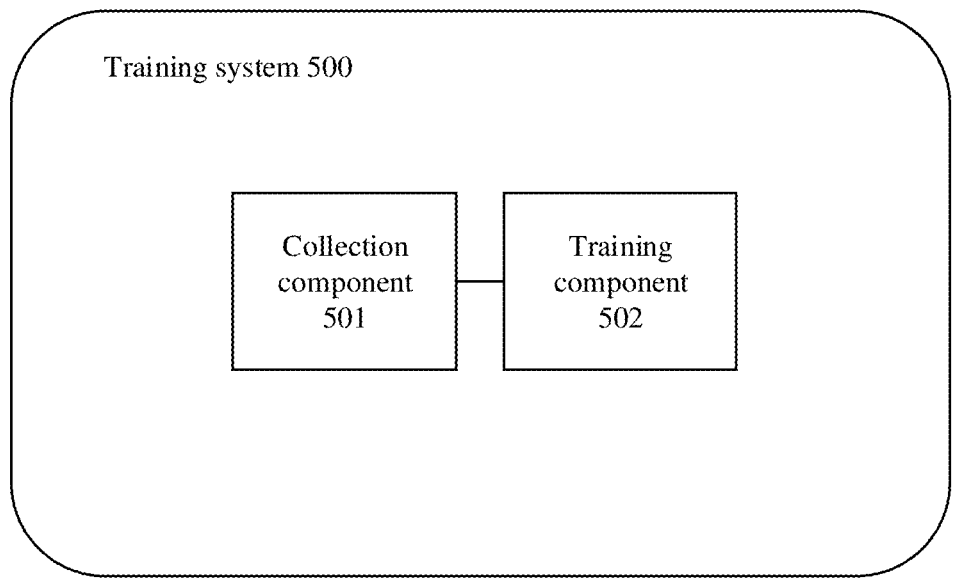
FIG. 5 is a schematic structural block diagram of a training system according to an embodiment of this application.

FIG. 5 is a schematic structural block diagram of a training system according to an embodiment of this application. The training system 500 shown in FIG. 5 includes a collection component 501 and a training component 502.

The collection component 501 may obtain a training data set (referred to as a training data set 1 in the following context) used to train an image quality prediction model, a small-sample image block set used to train a style transfer model, a training data set (referred to as a training data set 2 in the following context) used to train an image block classification model, a training data set (referred to as a training data set 3 in the following context) used to train a suspicious lesion component detection model, and a training data set (referred to as a training data set 4 in the following context) used to train a decision model.

The training component 502 may train an AI model by using a training data set obtained by the collection component 501, to obtain a corresponding AI model. For example, the training component 502 may first initialize a parameter at each layer of the image quality prediction model (namely, assign an initial value to each parameter), and then train the image quality prediction model by using a training image in the training data set 1, until a loss function in the image training prediction model converges or all training images in the training data set 1 are used for training.

It should be understood that, for a deployment manner and a deployment position of the training system, refer to a deployment manner and a deployment position of the pathological image processing system. The training system may further be deployed in a same environment or on a same device as a pathological image processing system, or may be deployed in a different environment or on a different device from a pathological image processing system. In another embodiment, the training system and the pathological image processing system may further constitute a system together.

Figure 6:
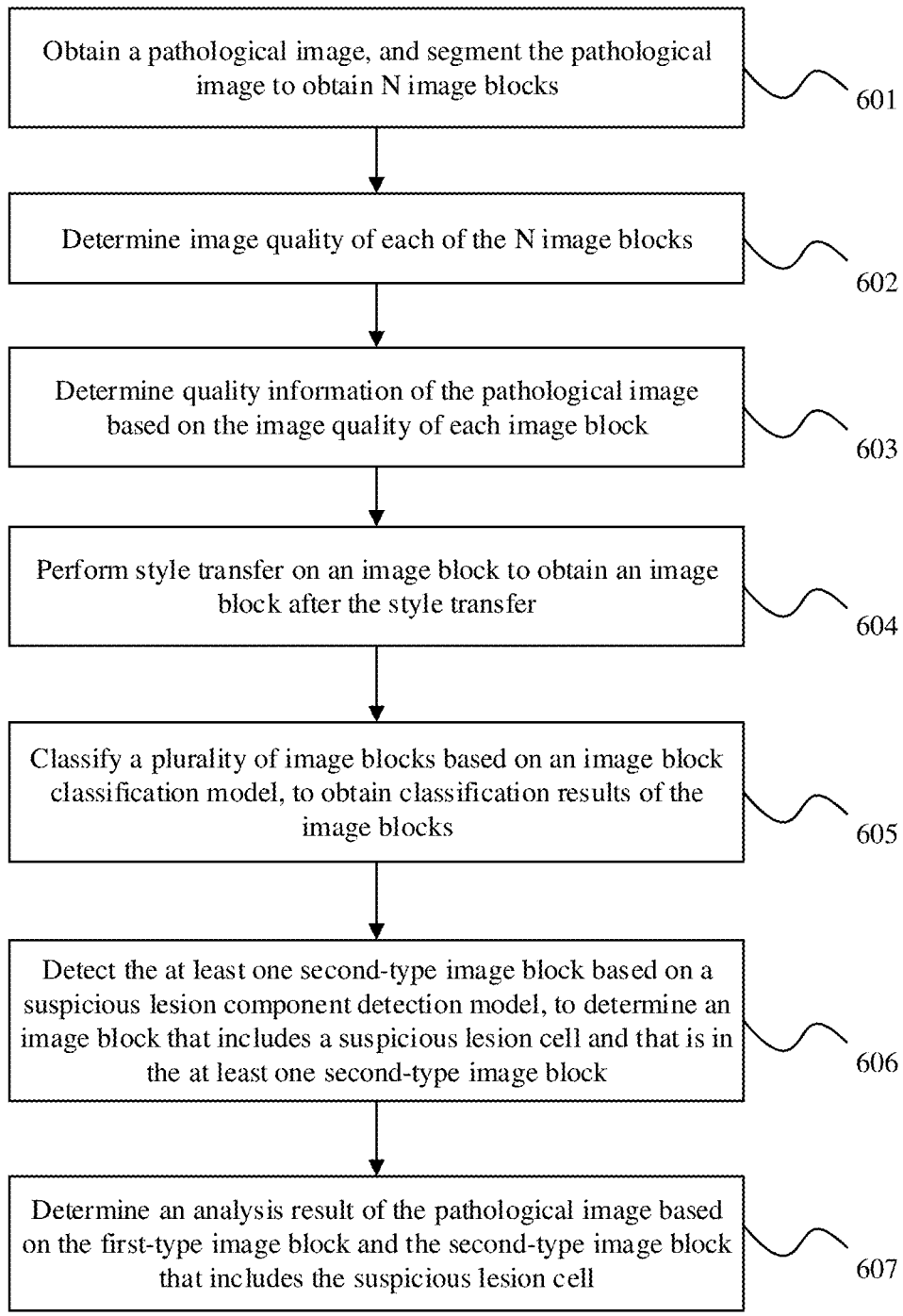
FIG. 6 is a schematic flowchart of an image processing method according to an embodiment of this application.

The following specifically describes an image processing method provided in an embodiment of this application with reference to FIG. 6. The method may be performed by the foregoing pathological image processing system.

FIG. 6 is a schematic flowchart of a pathological image processing method according to an embodiment of this application.

601: Obtain a pathological image, and segment the pathological image to obtain N image blocks, where N is a positive integer greater than or equal to 2.

602: Determine the image quality of each of the N image blocks.

The image quality of an image block may be one of a plurality of types of image quality. For example, in some embodiments, the image quality may be normal and abnormal. In this case, the image quality of each of the N image blocks may be normal or abnormal. In some other embodiments, the image quality of an image block may be normal, bubble, fade, and defocus. In this case, the image quality of each of the N image blocks may be any one of normal, bubble, fade, or defocus. In some embodiments, the image quality of an image block may include a plurality of levels. For example, the plurality of levels may be represented by excellent, good, average, and poor. For another example, the plurality of levels may be represented as scores, for example, 5, 4, 3, 2, and 1. The image quality of an image block with 5 scores is the best, and image quality of an image block with 1 score is the worst. In this case, the image quality of each of the N image blocks is one of the plurality of levels.

Optionally, in some embodiments, the image quality of the image block may be determined by using the image quality prediction model trained by the training system 500 shown in FIG. 5. For example, each of the N image blocks may be input to the image quality prediction model. The image quality prediction model is a trained AI model. The image quality of each of the N image blocks may be determined based on an output result of the image quality prediction model.

The following briefly describes how the training system 500 obtains the image quality prediction model through training. The training system 500 may train an initial image quality prediction model in a supervised learning manner, to obtain the image quality prediction model. The collection component 501 may collect a plurality of image blocks used for training. The plurality of image blocks may be obtained by segmenting one or more pathological images. The collected image blocks are processed and signed manually or by the collection component 501, to form one training data set 1. The training data set 1 may include a plurality of training images. Each of the plurality of training images may include one piece of image block data and label information. The image block data is data of one image block collected by the collection component 501 or data of one processed image block. The label information is actual image quality of the image block. The actual image quality of the image block may be manually pre-determined and marked. The training component 502 may train the initial image quality prediction model by using training data in the training data set 1, to obtain the image quality prediction model. For example, the training component 502 first initializes a parameter at each layer of the initial image quality prediction model (namely, assigns an initial value to each parameter), and then trains the initial image quality prediction model based on the training data in the training data set 1, until a loss function in the initial image quality prediction model converges or all training data in the training data set 1 is used for training. The training is completed, and the image quality prediction model that can be used in this solution is obtained.

The initial image quality prediction model may be some existing machine learning models or deep learning models that can be used for classification in the industry, such as, any one of a decision tree (DT), a random forest (RF), logistic regression (LR), a support vector machine (SVM), a convolutional neural network (CNN), a recurrent neural network (RNN), and the like.

Optionally, in some other embodiments, the image quality of each of the N image blocks may not be determined in an AI model-based manner. In other words, an artificial intelligence technology may not be used in a process of determining the image quality of each image block. For example, a definition of each image block may be determined by using Laplacian, a Brenner gradient function, a Tenengrad gradient function, and the like. If a definition of one image block meets a preset condition, it may be determined that image quality of the image block is normal; otherwise, it is determined that the image quality of the image block is abnormal. For another example, whether the image block is defocus may be determined based on an association between a pixel in the image block and a pixel around the pixel. If the association between the pixel in the image block and the pixel around the pixel is high (for example, greater than a preset association threshold), it may be determined that the image quality of the image block is defocus. If the association between the pixel in the image block and the pixel around the pixel is low (for example, less than a preset association threshold), it may be determined that the image quality of the image block is normal.

603: Determine quality information of the pathological image based on the image quality of each image block.

Optionally, in some embodiments, the quality information of the pathological image may include a quantity of image blocks whose image quality meets a preset standard in the N image blocks into which the pathological image is segmented. The quality information of the pathological image is an analysis result obtained after quality prediction is performed on each image block.

For example, if the image quality of image blocks is classified into normal and abnormal, image quality that meets the preset standard is normal. In this case, the quality information of the pathological image may include a quantity of image blocks whose image quality is normal.

For another example, if the image quality of image blocks is classified into normal, bubble, fade, and defocus, the image quality that meets the preset standard is normal. In this case, the quality information of the pathological image may include a quantity of image blocks whose image quality is normal.

For another example, if the image quality of image blocks is classified into a plurality of levels (for example, excellent, good, average, and poor), the image quality that meets the preset standard is image quality that is greater than or equal to one of the plurality of preset levels. For example, a preset level may be good. In this case, the quality information of the pathological image may include a total quantity of both image blocks whose image quality is excellent and image blocks whose image quality is good, or the quality information of the pathological image may include both a quantity of image blocks whose image quality is excellent and a quantity of image blocks whose image quality is good.

Optionally, in some embodiments, in addition to the quantity of image blocks whose image quality meets the preset standard, the quality information of the pathological image may further include a total quantity of image blocks. Therefore, a quantity of image blocks whose image quality does not meet the preset standard may be determined based on the total quantity of image blocks and the quantity of image blocks whose image quality meets the preset standard.

Optionally, in some other embodiments, the quality information of the pathological image may include a quantity of image blocks of each type/level of image quality.

For example, if the image quality of the image block is classified into normal and abnormal, the quality information of the pathological image may include a quantity of image blocks whose image quality is normal and a quantity of image blocks whose image quality is abnormal.

For another example, if the image quality of the image block is classified into normal, bubble, fade, and defocus, the quality information of the pathological image may include a quantity of image blocks whose image quality is normal, and a quantity of image blocks whose image quality is bubble, a quantity of image blocks whose image quality is fade and a quantity of image blocks whose image quality is defocus.

Optionally, in some other embodiments, the quality information of the pathological image may include identity information of an image block whose image quality meets the preset standard.

For example, the pathological image is segmented into P×Q image blocks, where P and Q are positive integers greater than or equal to 1, and P×Q is equal to N. Therefore, (p, q) may be used as identity information of an image block in a $p^{th}$ row and a $q^{th}$ column of the P×Q image blocks, where p is a positive integer greater than or equal to 1 and less than or equal to P, and q is a positive integer greater than or equal to 1 and less than or equal to Q.

It is assumed that the image quality of the image block is classified into normal and abnormal, and P×Q is equal to 3×3. If the quality information of the pathological image includes (1, 1), (1, 2), (2, 1), (3, 1), and (3, 2), it indicates image quality of an image block in a first row and a first column, an image block in a first row and a second column, an image block in a second row and a first column, an image block in a third row and a first column, and an image block in a third row and a second column in the 3×3 image blocks is normal.

Optionally, in some other embodiments, the quality information of the pathological image may include identity information of each type/level of image quality.

For example, it is assumed that the image quality of the image block is classified into normal and abnormal, and P×Q is equal to 3×3. If the quality information of the pathological image includes [(1, 1), (1, 2), (2, 1), (3, 1), and (3, 2)], [(1, 3), (2, 2), (2, 3), (3, 3)], it indicates image quantity of an image block in a first row and a first column, an image block in a first row and a second column, an image block in a second row and a first column, an image block in a third row and a first column, and an image block in a third row and a second column in the 3×3 image blocks is normal, and image quality of an image block in a first row and a third column, an image block in a second row and a second column, an image block in a second row and a third column, and an image block in a third row and a third column is abnormal.

604: Perform style transfer on an image block to obtain an image block after the style transfer. In another embodiment, the image block before the style transfer may alternatively be an initial image block, and the image block after the style transfer is referred to as an image block.

Optionally, in some embodiments, the style transfer may be performed only on the image block whose image quality meets the preset standard. For example, it is assumed that image quality of only $N_1$ image blocks in the N image blocks meets the preset standard, where $N_1$ is a positive integer greater than or equal to 1 and less than or equal to N. In this case, the style transfer may be performed on the $N_1$ image blocks to obtain $N_1$ transferred image blocks.

Optionally, in some other embodiments, the style transfer may be performed on the N image blocks obtained after the segmentation, to obtain N transferred image blocks. Then, the image block whose image quality meets the preset standard is selected from the N transferred image blocks for subsequent processing.

Optionally, in some other embodiments, the style transfer may be directly performed on a collected pathological image to obtain a transferred pathological image. Then the transferred pathological image is segmented to obtain N transferred image blocks.

Both a production reagent used in pathological image production and a scanning machine (or a camera) used in digital processing can affect a finally obtained pathological image. A model (for example, the image block classification model and/or a suspicious lesion component detection model) used during image block processing may be determined by using training data which is an image block obtained by segmenting a pathological image obtained by using one or more production reagents and one or more scanning machines (or cameras). A model used by an image analysis component may be obtained through training based on an image block with one style or several image blocks with similar styles. For ease of description, the following uses a style of an image block used to train the image analysis component as a target style. Styles of the N segmented image blocks obtained in the step 601 may be different from the target style. Therefore, if the style transfer is not performed on the image block, accuracy of subsequent image block classification and suspicious lesion cell detection is affected to some extent, and a final analysis result is affected. The style of the image block is converted into the target style, accuracy of a classification result of the image blocks and a detection result of the suspicious lesion cell can be improved, and the accuracy of the final analysis result of the pathological image can further be improved.

For ease of description, it is assumed in the following that style transfer needs to be performed on the $N_1$ image blocks whose quality meets the preset standard.

Optionally, in some embodiments, the style transfer may be determined by using the style transfer model trained by the training system 500 shown in FIG. 5. For example, each of the $N_1$ image blocks may be input to the style transfer model. The style transfer model is a trained AI model. $N_1$ transferred image blocks may be obtained based on an output result of the style transfer model.

The following briefly describes how the training system 500 trains the style transfer model. The training system 500 may train the style transfer model in an unsupervised learning manner. The style transfer model can be the AI model. A structure of the style transfer model is not limited in embodiments of this application. For example, the style transfer model may be any model in a generative adversarial network (GAN) framework, for example, a deep convolutional generative adversarial network (DCGAN), or another AI model that generates an image block based on a feature of each image block in a small-sample image block set. An image block in the small-sample image block set is collected by the collection component 501. A style of the image block in the small-sample image block set is the target style of the style transfer.

The following describes a principle of a GAN.

The GAN includes a generator G and a discriminator D. The generator G is configured to generate a candidate image block set based on input of the GAN. The discriminator D is connected to an output end of the generator G, and is configured to discriminate whether the candidate image block set output by the generator G is a real image block set.

In the GAN, the generator G and the discriminator D are in an alternate adversarial training process. Any image block set is used as input of the generator G. The generator G outputs the candidate image block set. The discriminator D uses the candidate image block set generated by the generator G and the small-sample image block set as input values, compares features of the candidate image block set and the small-sample image block set, and outputs a probability that the candidate image block set and the small-sample image block set belong to image block sets of a same type (the candidate image block set whose type is the same as a type of the small-sample image block set is also referred to as the real image block set, and the real image block set and the small-sample image block set have a same or similar feature). A parameter in the generator G is optimized based on the probability that the output candidate image block set is the real image block set (in this case, a parameter in the discriminator D remains unchanged) until the candidate image block set output by the generator G is discriminated by the discriminator D to be the real image block set (the probability that the candidate image block set is the real image block set is greater than a threshold). The discriminator D optimizes a parameter at each network layer inside based on the probability output by the discriminator D (in this case, the parameter in the generator G remains unchanged). Therefore, the discriminator D can continue to discriminate that the candidate image block set output by the generator G and the small-sample image block set do not belong to a same type. Parameters in the generator G and the discriminator D are alternately optimized until the generator G generates a candidate image block set that cannot be discriminated by the discriminator D as a real signal set. It can be learned from the training process that, the process in which the generator G and the discriminator D are alternately trained is a process in which the generator G and the discriminator D run in competition with each other. When the candidate image block set that can be generated by the generator G has the same or similar feature with the small-sample image block set, namely, when the candidate image block set is close to the real image block set, the discriminator D cannot accurately discriminate whether the input image block set is the real image block set, and GAN training is completed.

Optionally, in some embodiments, the step 604 may not be performed. For example, a style of the pathological image obtained in the step 601 is the same as or similar to the target style. In this case, the style transfer may not be performed on the image block. For another example, the model used to classify the image block and detect the suspicious lesion cell may adapt to image blocks of various styles. Therefore, the style transfer may not be performed on the image block.

Optionally, in some embodiments, the step 602 and the step 603 may not be performed. In this case, the style transfer may be directly performed on the N image blocks obtained by segmenting the pathological image (namely, the step 604 is performed), or classification and a subsequent step may be directly performed (namely, steps 605 to 607).

Figure 7:
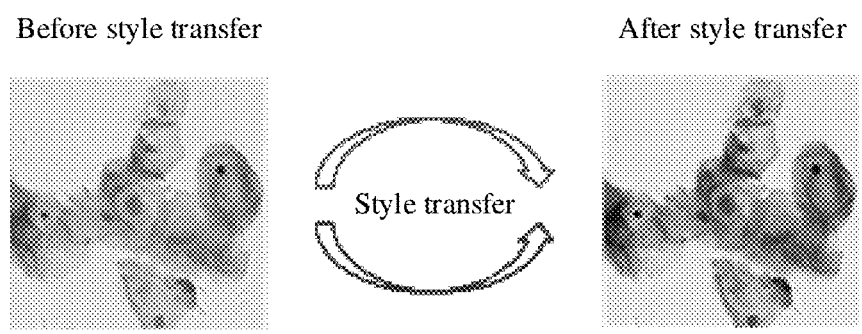
FIG. 7 shows an image block before style transfer and an image block after style transfer according to an embodiment of this application.

FIG. 7 shows an image block before style transfer and an image block after style transfer. A color depth and a contrast of the image block after the style transfer change.

605: Classify a plurality of image blocks based on the image block classification model, to obtain classification results of the image blocks.

Specifically, the classification result of the image blocks indicates that a type of each of the plurality of image blocks is a first type or a second type. An image block of the first type is referred to as a first-type image block. An image block of the second type is referred to as a second-type image block.

Optionally, in some embodiments, there may be one or more first-type image blocks. A quantity of suspicious lesion cells in the first-type image block is greater than or equal to a first preset quantity threshold. A quantity of suspicious lesion cells in the second-type image block is less than the first preset quantity threshold.

Optionally, in some other embodiments, an area of a suspicious lesion cell in the first-type image block is greater than or equal to a first preset area threshold. An area of a suspicious lesion cell in the second-type image block is less than the first preset area threshold.

Optionally, in some other embodiments, a quantity or an area of suspicious lesion cells in the first-type image block is greater than a preset threshold, and a quantity or an area of suspicious lesion cells in the second-type image block is less than the preset threshold. The preset threshold may include a first preset quantity and a first preset area threshold.

Optionally, in some embodiments, one image block is the first-type image block provided that a quantity of suspicious lesion cells in the image block is greater than or equal to the first preset quantity threshold or an area of a suspicious lesion cell is greater than or equal to the first preset area threshold. In other words, one image block is the second-type image block provided that a quantity of suspicious lesion cells is less than the first preset quantity threshold and an area of a suspicious lesion cell is less than the first preset area threshold.

Optionally, in some other embodiments, one image block is the second-type image block provided that a quantity of suspicious lesion cells in the image block is less than the first preset quantity threshold or an area of a suspicious lesion cell is less than the first preset area threshold. In other words, one image block is the first-type image block provided that a quantity of suspicious lesion cells is greater than or equal to the first preset quantity threshold and an area of a suspicious lesion cell is greater than or equal to the first preset area threshold.

It may be understood that, if the step 604 is performed, the plurality of image blocks in the step 605 are the image blocks obtained after the style transfer is performed.

In the step 605, the image blocks are classified into the first-type image block and the second-type image block based on the quantity of suspicious lesion cells and/or the area of the suspicious lesion cell. In some other embodiments, the image blocks may further be classified into a first-type image block, a second-type image block, and a third-type image block based on the quantity of suspicious lesion cells and/or the area of the suspicious lesion cell.

For example, in some embodiments, two preset quantities: a first preset quantity and a second preset quantity, may be set. The first preset quantity is greater than the second preset quantity. If a quantity of suspicious lesion cells in one image block is greater than or equal to the first preset quantity, the image block is the first-type image block. If a quantity of suspicious lesion cells in one image block is less than the first preset quantity and is greater than or equal to the second preset quantity, the image block is the second-type image block. If a quantity of suspicious lesion cells in one image block is less than the second preset quantity, the image block is the third-type image block.

For another example, in some other embodiments, only one preset quantity may be set, for example, the first preset quantity. In this case, if a quantity of suspicious lesion cells in one image block is greater than or equal to the first preset quantity, the image block is the first-type image block. If there is no suspicious lesion cell in one image block, the image block is the second image block. If there is a suspicious lesion cell in one image block and a quantity of the suspicious lesion cells is less than the first preset quantity, the image block is the third-type image block.

Optionally, in some embodiments, image block classification may be determined by using the image block classification model trained by the training system 500 shown in FIG. 5. For example, the plurality of image blocks may be input to the image block classification model. The image block classification model is a trained AI model. The first-type image block and the at least one second-type image block are obtained based on an output result of the image block classification model.

The following briefly describes how the training system 500 trains the image block classification model. For ease of description, the following assumes that the first-type image block and the second-type image block are classified based on the quantity of suspicious lesion cells. The training system 500 may train the image block classification model in a supervised learning manner. The collection component 501 may collect a plurality of image blocks. The plurality of image blocks may be obtained by segmenting one or more pathological images. Collected image blocks are signed by a doctor to form a training data set (referred to as a training data set 2 in the following context). The training data set 2 may include a plurality of pieces of training data. Each of the plurality of pieces of training data may include one piece of image block data and label information. The image block data is data of one image block collected by the collection component 501 or data of one processed image block. The label information is an actual type of the image block (namely, the first-type image block or the second-type image block).

Optionally, in some embodiments, a collected image block may be marked by a doctor or a pathologist. The doctor may determine whether the image block is the first-type image block or the second-type image block based on the quantity of suspicious lesion cells in the image block, and use a determining result as label information of the image block.

Optionally, in some other embodiments, a collected image block may be independently marked by two or more doctors or pathologists. Label information of the image block is obtained based on mark results of the two or more doctors or pathologists. For example, in some embodiments, if two doctors of three doctors determine that one image block is the first-type image block, and the other doctor determines that the image block is the second-type image block, it may be determined that the label information of the image block may be the first-type image block. For another example, in some other embodiments, if two doctors of three doctors determine that one image block is the first-type image block, and the other doctor determines that the image block is the second-type image block, a fourth doctor may determine a type of the image block. A result determined by the fourth doctor is used as mark information of the image block. Therefore, accuracy of the training data can be improved.

Optionally, in some embodiments, the image blocks in the training data set 2 are image blocks of a same style or a similar style.

The training component 502 may train an initial image block classification model by using the training data in the training data set 2, to obtain the image block classification model. For example, the training component 502 first initializes a parameter at each layer of the initial image block classification model (namely, assigns an initial value to each parameter), and then trains the initial image block classification model based on the training data in the training data set, until a loss function in the initial image block classification model converges or all training data in the training data set 2 is used for training. The training is completed, and a trained model is referred to as the image block classification model.

The initial image block classification model may be some existing machine learning models or deep learning models that can be used for image classification in the industry, such as, residual networks (ResNets), visual geometry group (VGG) networks, Google networks (GoogLeNet) and inception networks.

It is assumed that the image classification model is determined after being trained based on an inception network version 1 (Inception Version 1, Inception-v1). In this case, the image classification model may include an input module, an inception module, and an output module. The input module performs the following processing on input data (namely, a to-be-classified image block): 7×7 convolution, 3×3 pooling, local response normalization (LRN), 1×1 convolution, 3×3 convolution, and LRN, to obtain processed data. Then, the processed data may pass through a plurality of (for example, nine) inception modules. The output module may perform average pooling (AP), fully connected (FC), and softmax activation on the data processed by the inception module, to obtain an output result. The output result obtained after being processed by the output module is a type of the to-be-classified image block.

606: Detect the at least one second-type image block based on the suspicious lesion component detection model, to determine an image block that includes a suspicious lesion cell and that is in the at least one second-type image block.

Optionally, in some embodiments, the suspicious lesion cell detection may be determined by using the suspicious lesion component detection model trained by the training system 500 shown in FIG. 5. The at least one second-type image block may be input to the suspicious lesion component detection model. The suspicious lesion component detection model detects a suspicious lesion cell in each second-type image block, determines a location of the suspicious lesion cell in the second-type image block, and obtains a detection result. The detection result includes location information of the detected suspicious lesion cell in a corresponding second-type image block. The suspicious lesion component detection model is a trained AI model. The suspicious lesion component detection model may output the location information of the suspicious lesion cell. The image block, including the suspicious lesion cell, in the at least one second-type image block may be determined based on the location information of the suspicious lesion cell.

The following briefly describes how the training system 500 trains the suspicious lesion component detection model. The training system 500 may train the suspicious lesion component detection model in a supervised learning manner. The collection component 501 may collect a plurality of image blocks. The plurality of image blocks may be obtained by segmenting one or more pathological images. Collected image blocks are signed by a doctor to form a training data set (referred to as a training data set 3 in the following context). The training data set 3 may include a plurality of pieces of training data. Each of the plurality of pieces of training data may include one piece of image block data and label information. The image block data is data of one image block collected by the collection component 501 or data of one processed image block. The label information is the location of the suspicious lesion cell in the image block.

Optionally, in some embodiments, a collected image block may be marked by a doctor or a pathologist. The doctor may identify and determine whether the image block includes the suspicious lesion cell. If the image block includes the suspicious lesion cell, the location of the suspicious lesion cell may be marked to obtain the label information of the image block.

Optionally, in some other embodiments, a collected image block may be independently marked by two or more doctors or pathologists. Label information of the image block is obtained based on mark results of the two or more doctors or pathologists. Optionally, in some embodiments, if a detection evaluation function intersection-over-union (IoU) is greater than a preset threshold (for example, 0.3) 3, a plurality of boundary boxes having a consistent lesion type, diagnosed by a plurality of doctors are combined into an average boundary box. In other words, a boundary box marked by only one doctor may be skipped to maintain high quality, and the combined boundary box and the lesion type are final markers on the cell. Optionally, in some other embodiments, if results marked by a plurality of doctors are different, another more experienced doctor may mark the location of the suspicious lesion cell in the image block. A result marked by the doctor is used as mark information of the image block.

The suspicious lesion component detection model may be some existing machine learning models or deep learning models that can be used for object detection in the industry, such as, any one of a convolutional neural network (CNN), a region-based convolutional neural network (R-CNN), a fast-RCNN, a faster-RCNN, a single shot multibox detector (SSD), and the like.

The training component 502 may obtain the suspicious lesion component detection model by using training data in the training data set 3. The following uses the faster-RCNN as an example to briefly describe a training process and a use process of the suspicious lesion component detection model.

The training process of the suspicious lesion component detection model:

A region proposal network (RPN) is obtained by using the training data in the training data set 3. A plurality of proposals are obtained through the RPN. The fast-RCNN (the Fast-RCNN may be considered as one initial suspicious lesion component detection model) is trained by using the plurality of proposals. The trained fast-RCNN is the suspicious lesion component detection model.

The use process of the suspicious lesion component detection model:

A to-be-detected second-type image block is input into the suspicious lesion component detection model. The suspicious lesion component detection model may include four modules: a convolution module, an RPN module, a region of interest (ROI) pooling module, and a classification module. The convolution module is configured to extract a feature (feature map) of the second-type image block. The RPN module is configured to generate a suggested region (region proposal). The ROI pooling module is configured to collect the feature extracted by the convolution module and the suggested region generated by the PRN module, and extract a suggested feature (proposal feature map) based on collected information. The classification module calculates suggested classification based on the suggested feature extracted by the ROI pooling module, and performs bounding box regression to obtain a location of the suspicious lesion cell in the second-type image block.

607: Determine the analysis result of the pathological image based on the first-type image block and the second-type image block that includes the suspicious lesion cell.

Optionally, in some embodiments, that the analysis result of the pathological image is determined based on the first-type image block and the second-type image block that includes the suspicious lesion cell may include that the analysis result of the pathological image is determined based on the first-type image block, the second-type image block including the suspicious lesion cell, and the quality information of the pathological image.

For ease of description, the following assumes that the image quality of the image block is classified into four types: normal, bubble, fade, and defocus, and that the image block that meets the preset standard is the image block whose image quality is normal. A ratio of the image block whose image quality is normal to all image blocks may be determined based on the image quality information. For ease of description, a letter R is used in the following to indicate the ratio of the quantity of image blocks whose image quality is normal to the total quantity of image blocks.

In some embodiments, whether the pathological image is available may be determined based on R.

For example, in some embodiments, if R is less than a preset ratio, it may be directly determined that the analysis result of the pathological image is that the pathological image is unavailable. In other words, the N image blocks obtained by segmenting the pathological image do not have enough image blocks that meet a quality requirement. In this way, the final result obtained based on the pathological image is also unreliable. If R is greater than the preset ratio, it may be determined that the pathological image is available, and the analysis result of the pathological image continues to be determined based on the classification result of the image blocks and the detection result of the suspicious lesion cell. Optionally, in some embodiments, whether the pathological image is available may be first determined based on the quality information of the pathological image. If the pathological image is unavailable, the segmented image block is not further processed, and the analysis result is directly output. The analysis result is that the pathological image is unavailable. If the pathological image is available, the image block whose image quality is normal may be classified and the suspicious lesion cell may be detected, and the analysis result of the pathological image is determined based on the classification result of the image blocks and the detection result of the suspicious lesion cell.

In some other embodiments, a confidence level of the analysis result of the pathological image may be determined based on R, or based on R, the first-type image block, and the second-type image block that includes the suspicious lesion cell.

Optionally, in some embodiments, the analysis result of the pathological image may be determined based on the first-type image block and the second-type image block that includes the suspicious lesion cell. For ease of description, the first-type image block and the second-type image block that includes the suspicious lesion cell are collectively referred to as classification result information of the image block below.

Optionally, in some embodiments, it may be determined, based on a correspondence between the classification result information of the image block and a decision result, that the analysis result of the pathological image is a decision result corresponding to the classification result information of the image block, in a plurality of decision results. For example, Table 1 shows one example correspondence between classification result information of the image block and a decision result.

TABLE 1

| Num1 | Num2 | Num3 | Decision result |
|---|---|---|---|
| Num1 < T11 | Num2 > T21 | Num3 < T31 | Decision result 1 |
| T11 ≤ Num1 < T12 | T21 ≥ Num2 > T22 | T31 ≤ Num3 < T32 | Decision result 2 |
| T12 ≤ Num1 | T22 ≥ Num2 | T32 ≤ Num3 | Decision result 3 |

In Table 1, T11, T12, T13, T21, T22, T31, and T32 represent different preset thresholds. Num1 represents a quantity of first-type image blocks. Num2 represents a quantity of second-type image blocks. Num3 represents a total quantity of suspicious pathological cells in the second-type image blocks.

For example, as shown in Table 1, if the quantity of first-type image blocks is less than a preset threshold T11, the quantity of second-type image blocks is greater than a preset threshold T21, and the total quantity of suspicious lesion cells in the second-type image block is less than a preset threshold T31, the analysis result of the pathological image is a decision result 1.

Optionally, in some other embodiments, it may be determined, based on R, a correspondence between the classification result information of the image block and a decision result, that the analysis result of the pathological image is a decision result corresponding to the classification result information of the image block and R, in a plurality of decision results. For example, Table 2 shows one example correspondence between classification result information of the image block and a decision result.

TABLE 2

| Num1 | Num2 | Num3 | R | Decision result |
|---|---|---|---|---|
| Num1 < T11 | Num2 > T21 | Num3 < T31 | R ≥ T41 | Decision result 1 |
| T11 ≤ Num1 < T12 | T21 ≥ Num2 > T22 | T31 ≤ Num3 < T32 | T42 ≤ R < T41 | Decision result 2 |
| T12 ≤ Num1 | T22 ≥ Num2 | T32 ≤ Num3 | T43 ≤ R < T42 | Decision result 3 |
| — | — | — | R < T43 | Decision result 4 |

In Table 2, T11, T12, T13, T21, T22, T31, T32, T41, T42, and T43 represent different preset thresholds. Num1 represents a quantity of first-type image blocks. Num2 represents a quantity of second-type image blocks. Num3 represents a total quantity of suspicious lesion cells in the second-type image blocks. R represents a ratio of a quantity of image blocks whose labels are normal to a total quantity of image blocks.

For example, as shown in Table 2, if the quantity of first-type image blocks is less than a preset threshold T11, the quantity of second-type image blocks is greater than a preset threshold T21, the total quantity of suspicious lesion cells in the second-type image block is less than a preset threshold T31, and R is greater than or equal to a threshold T41, the analysis result of the pathological image is a decision result 1.

For another example, as shown in Table 2, if R is less than a preset threshold T43, the quantity of first-type image blocks, the quantity of second-type image blocks, and the total quantity of suspicious lesion cells in the second-type image block may not be determined, and the analysis result of the pathological image is directly determined as a decision result 4.

It may be understood that Table 1 and Table 2 are merely an example schematic diagram of the correspondence between the classification result information of the image block and the decision result, or of the correspondence between R, the classification result information of the image block, and the decision result. The correspondence between the classification result information of the image block and the decision result, or the correspondence between R, the classification result information of the image block, and the decision result is not limited in embodiments of this application. For example, in some embodiments, the correspondence between the classification result of the image blocks and the decision result may further include an average suspicious lesion cell in the second-type image block, a ratio of the quantity of the first-type image blocks to a total quantity of image blocks that meet the quality requirement (namely, a sum of the quantity of the first-type image blocks and the quantity of the second-type image blocks), or a ratio of the quantity of the second-type image blocks to a total quantity of image blocks that meet the quality requirement, or the like.

Optionally, in some other embodiments, the analysis result of the pathological image may be determined by using the decision model trained by the training system 500 shown in FIG. 5. For example, R and the classification result information of the image block, or the classification result information of the image block may be input to the decision model. The decision model is a trained AI model, and the decision model outputs the analysis result of the pathological image.

The following briefly describes how the training system 500 trains the decision model. The training system 500 may train the decision model in a supervised learning manner. The collection component 501 may collect a plurality of pathological images. Collected image blocks are signed by a doctor to form a training data set (referred to as a training data set 4 in the following context). The training data set 4 may include a plurality of pieces of training data. Each of the plurality of pieces of training data may include pathological image data and label information. The pathological image is data of a plurality of image blocks obtained by segmenting one pathological image collected by the collection component 501 or data of a plurality of processed image blocks. The label information is a decision result corresponding to the pathological image, determined by the doctor or a pathologist based on the pathological image.

Optionally, in some embodiments, the doctor or the pathologist may determine the decision result of the pathological image based on the collected pathological image, and use the decision result as the label information.

Optionally, in some other embodiments, a plurality of doctors or pathologists may independently determine the decision result of the pathological image based on the collected pathological image, determine a final decision result of the pathological image with reference to the plurality of decision results, and use the decision result as the label information.

Optionally, in some embodiments, the plurality of pathological images that are collected by the collection component 501 and that are used to train the decision model have a same or similar style.

Optionally, in some embodiments, the pathological image data included in the training data may include classification result information of the plurality of image blocks that meet the quality requirement, of the pathological image.

Optionally, in some other embodiments, the pathological image data included in the training data may include classification result information of the plurality of image blocks that meet the quality requirement, of the pathological image and quality information of the pathological image.

Optionally, in some embodiments, the classification result information of the image block and/or the quality information of the pathological image included in the training data may be determined by using the trained AI model.

Optionally, in some other embodiments, the classification result information of the image block and/or the quality information of the pathological image included in the training data may be determined manually.

The training component 502 may obtain the decision model by using the training data in the training data set 4. For example, the training component 502 first initializes a parameter at each layer of an initial decision model (namely, assigns an initial value to each parameter), and then trains the initial decision model based on the training data in the training data set, until a loss function in the initial decision model converges or all training data in the training data set 4 is used for training. A trained initial decision model is referred to as the decision model.

The initial decision model may be some existing machine learning models or deep learning models that can be used for classification in the industry, such as, any one of a decision tree (DT), a random forest (RF), logistic regression (LR), a support vector machine (SVM), a convolutional neural network (CNN), a recurrent neural network (RNN), faster R-CNN (Faster Region-CNN), a single shot multibox detector (SSD), and the like.

Further, TCT cervical cancer cell detection is used as an example. In some embodiments, the analysis result of the pathological image may include one or both of a squamous epithelial lesion analysis result and/or a glandular cell analysis result, or the pathological image is unavailable. The squamous epithelial lesion analysis result includes an atypical squamous epithelial cell-unspecific meaning, an atypical squamous epithelial cell-not excluding a high-grade intraepithelial lesion, a low-grade intraepithelial lesion, a high-grade intraepithelial lesion, or a squamous cell carcinoma. The glandular cell analysis result includes an atypical glandular cell-nonspecific, an atypical glandular cell-prone to canceration, or adenocarcinoma.

This application further provides an example data processing apparatus. It should be understood that a function included in the data processing apparatus may be the same as a function included in the pathological image processing system, or the data processing apparatus may include some functions of the pathological image processing system. Alternatively, the data processing apparatus may further include some or all functions of the pathological image processing system and some or all functions of the training system.

Figure 8:
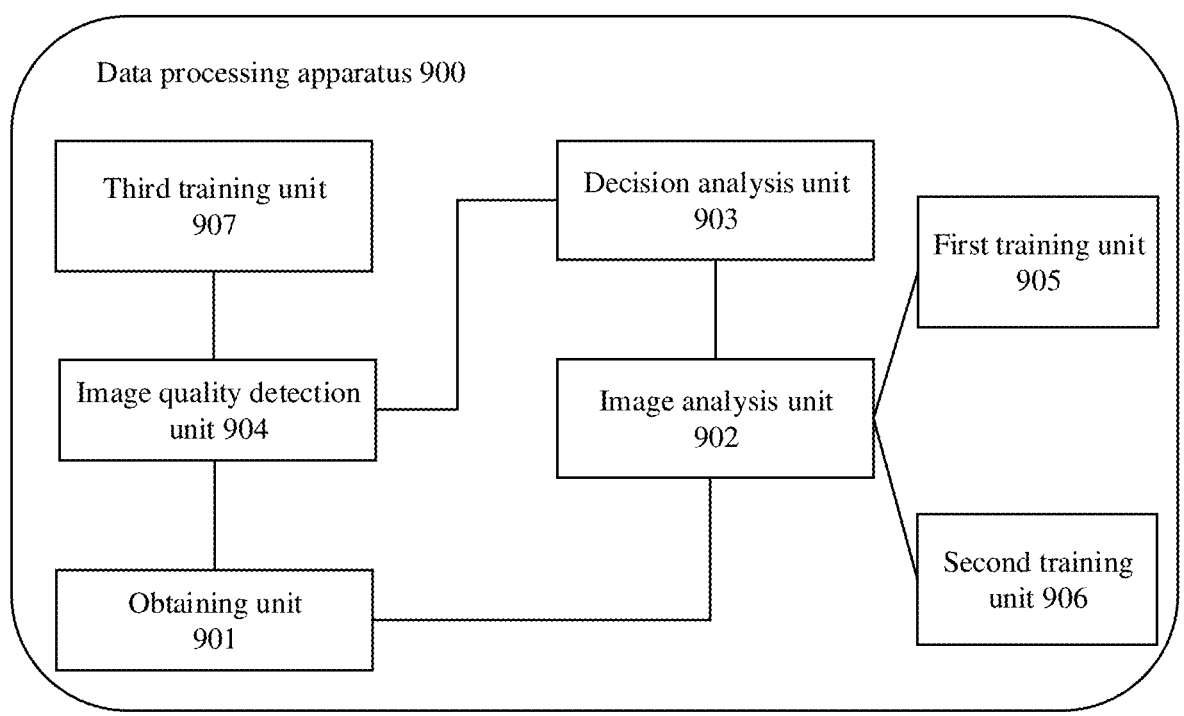
FIG. 8 is a schematic structural block diagram of a data processing apparatus according to an embodiment of this application.

FIG. 8 is a schematic structural block diagram of a data processing apparatus according to an embodiment of this application. The data processing apparatus 900 shown in FIG. 8 includes an obtaining unit 901, an image analysis unit 902, and a decision analysis unit 903.

The obtaining unit 901 is configured to obtain a plurality of image blocks. The plurality of image blocks are obtained by segmenting a to-be-analyzed pathological image.

The image analysis unit 902 is configured to input the plurality of image blocks to a first analysis model to obtain a first analysis result. The first analysis model classifies each of the plurality of image blocks based on a quantity or an area of suspicious lesion components. The first analysis result indicates that a type of each image block is a first type or a second type. The first type indicates that a quantity or an area of suspicious lesion components in the image block is greater than or equal to a preset threshold. The second type indicates that the quantity or the area of the suspicious lesion components in the image block is less than the preset threshold. The first analysis model may be the image block classification model in the method embodiment. The first analysis result is the classification result of the image blocks in the method embodiment.

The image analysis unit 902 is further configured to input at least one second-type image block in the first analysis result to a second analysis model to obtain a second analysis result. The second analysis model analyzes a location of a suspicious lesion component of each input second-type image block. The second analysis model may be the suspicious lesion component detection model in the method embodiment. The second analysis result is the detection result in the method embodiment.

The decision analysis unit 903 is configured to obtain a final analysis result of the pathological image based on the first analysis result and the second analysis result.

Optionally, in some embodiments, the apparatus further includes an image quality detection unit 904, configured to input each image block to a third analysis model to obtain a third analysis result. The third analysis model predicts image quality of each image block. The decision analysis unit 903 is further configured to obtain the final analysis result of the pathological image based on the first analysis result, the second analysis result, and the third analysis result. The third analysis model may be the image quality prediction model in the method embodiment. The second analysis result is the quality information in the method embodiment.

Optionally, in some embodiments, the obtaining unit 901 is further configured to obtain a plurality of initial image blocks formed after the to-be-analyzed pathological image is segmented, and input each of the plurality of initial image blocks to a style transfer model to obtain the plurality of image blocks. The style transfer model converts a style of each initial image block.

Optionally, in some embodiments, the apparatus further includes a first training unit 905, configured to train an initial first analysis model based on a first training data set to obtain the first analysis model. The initial first analysis model is one of artificial intelligence AI models. The first training data set includes a plurality of first training images. A label of each first training image is a first type or a second type.

Optionally, in some embodiments, the apparatus further includes a second training unit 906, configured to train an initial second analysis model based on the second training data set to obtain the second analysis model. The initial second analysis model is one of the artificial intelligence AI models. The second training data set includes a plurality of second training images including a suspicious lesion component. A label of each second training image is location information of the suspicious lesion component in the training image.

Optionally, in some embodiments, the apparatus further includes a third training unit 907, configured to train an initial third analysis model based on the third training data set to obtain the third analysis model. The initial third analysis model is one of the artificial intelligence AI models. The third training data set includes a plurality of third training images. A label of each third training image is an image quality type of each third training image.

Optionally, in some embodiments, the decision analysis unit 903 is further configured to input the first analysis result and the second analysis result to a decision model to obtain the final analysis result of the pathological image.

For specific functions and beneficial effects of the obtaining unit 901, the image analysis unit 902, the decision analysis unit 903, the image quality detection unit 904, the first training unit 905, the second training unit 906, and the third training unit 907, refer to descriptions in the method embodiment. For example, the image analysis unit 902 may perform the step 605 and the step 606. The decision analysis unit 903 may perform the step 607. The image quality detection unit 904 may perform the step 602 and the step 603.

It may be understood that the described apparatus embodiment is merely an example. For example, division into the modules is merely logical function division and may be other division in an actual implementation. For example, the image analysis unit 902 may be collectively described as an image analysis component. The decision analysis unit 903 may be described as a decision analysis component. The obtaining unit 901 may be further divided into a collection unit and a style transfer unit. The collection unit may be described as an image collection component. The style transfer unit and the image quality detection unit 904 may be collectively described as an image preprocessing component. The first training unit 905, the second training unit 906, and the third training unit 907 may be collectively described as a training system.

Optionally, in some embodiments, units in the data processing apparatus 900 shown in FIG. 8 may be implemented by using different devices. For example, the first training unit 905, the second training unit 906, and the third training unit 907 may be implemented by using an independent training device. The training device may send a trained model to the data processing apparatus 900.

This application further provides a computing device 400 shown in FIG. 4. A processor 402 in the computing device 400 reads executable code stored in a memory 404, to perform the pathological image processing method.

Figure 9:
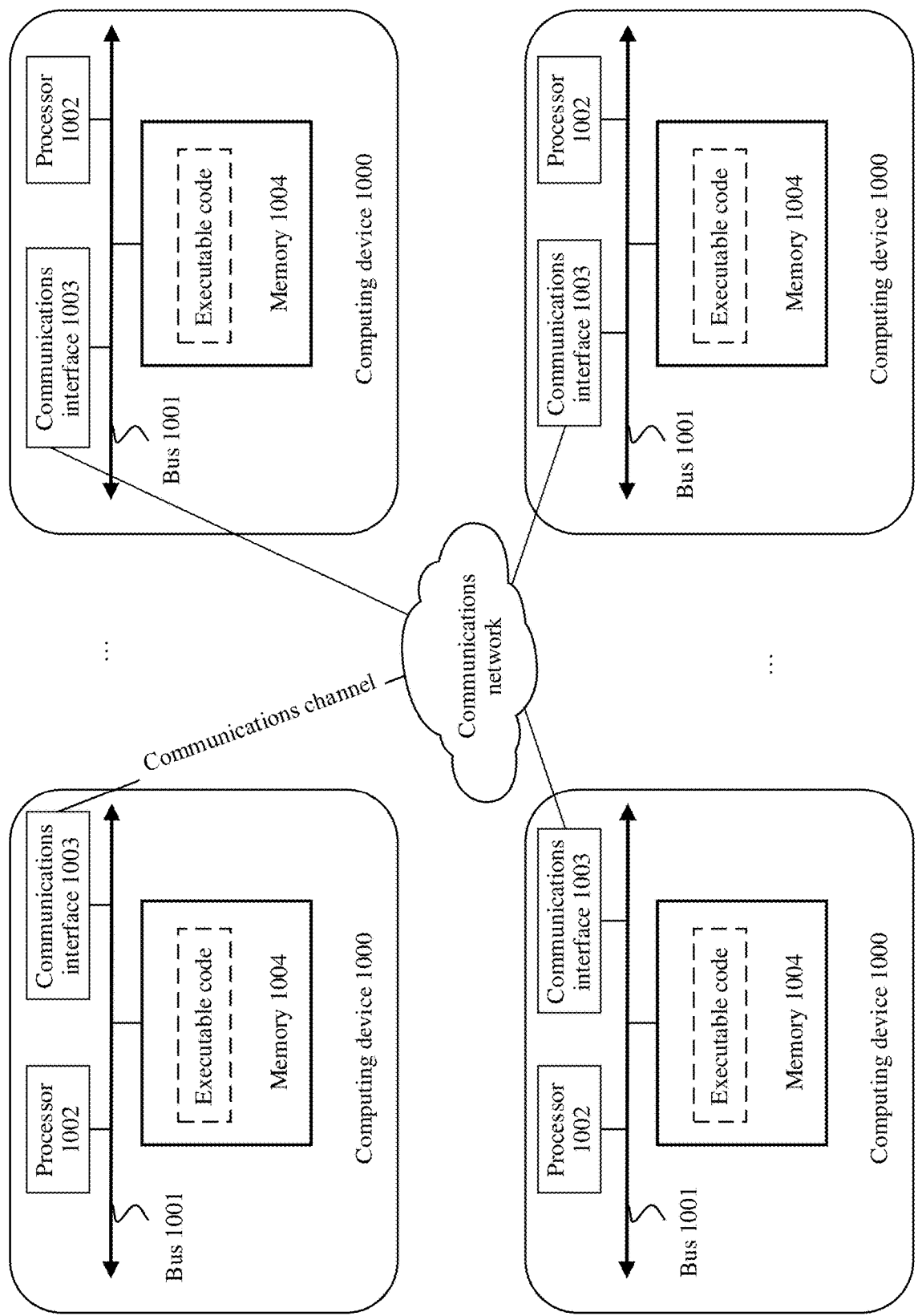
FIG. 9 is a schematic structural block diagram of a computing device system according to an embodiment of this application.

Because the units in the data processing apparatus 900 in this application may be respectively deployed on a plurality of computing devices, this application further provides a computing device system shown in FIG. 9. The computing device system includes a plurality of computing devices 1000. Each computing device 1000 includes a bus 1001, a processor 1002, a communications interface 1003 and a memory 1004. The processor 1002, the memory 1004, and the communications interface 1003 communicate with each other through the bus 1001.

The processor 1002 may be a CPU. The memory 1004 may include a volatile memory, for example, a RAM. The memory 1004 may further include a non-volatile memory, such as a ROM, a flash memory, an HDD, or an SSD. The memory 1004 stores executable code. The processor 1002 executes the executable code to perform some image processing methods. The memory 1004 may further include another software module, for example, an operating system, for running a process. The operating system may be Linux™, Unix™, Windows™, or the like.

A communications channel is established between the computing devices 1000 through a communications network. Each computing device 1000 runs any one or more of an obtaining unit 901, an image analysis unit 902, a decision analysis unit 903, an image quality detection unit 904, a first training unit 905, a second training unit 906, and a third training unit 907. Any computing device 1000 may be a computing device in a cloud data center, a computing device in an edge data center, or a terminal computing device.

A description of a procedure corresponding to each of the accompanying drawings has a focus. For a part that is not described in detail in a procedure, refer to a related description of another procedure.

All or some of the foregoing embodiments may be implemented by using software, hardware, firmware, or any combination thereof. When software is used to implement the embodiments, all or some of the embodiments may be implemented in a form of a computer program product. The computer program product includes one or more computer instructions. When the computer program instructions are loaded and executed on a computer, all or some of the procedures or functions according to FIG. 6 in the embodiments of the present invention are generated.

Based on the method provided in the embodiments of this application, this application further provides a computer program product. The computer program product includes computer program code. When the computer program code is run on a computer, the computer is enabled to perform the method in any one of the embodiments shown in FIG. 6.

Based on the method provided in the embodiments of this application, this application further provides a non-transitory computer readable storage medium. The non-transitory computer readable storage medium stores program code. When the program code is run on a computer, the computer is enabled to perform the method in any one of the embodiments shown in FIG. 6.

A person of ordinary skill in the art may be aware that, in combination with the examples described in the embodiments disclosed in this specification, units and algorithm steps may be implemented by electronic hardware or a combination of computer software and electronic hardware. Whether the functions are performed by hardware or software depends on particular applications and design constraint conditions of the technical solutions. A person skilled in the art may use different methods to implement the described functions for each particular application, but it should not be considered that the implementation goes beyond the scope of this application.

It may be clearly understood by a person skilled in the art that, for the purpose of convenient and brief description, for a detailed working process of the system, apparatus, and unit, refer to a corresponding process in the method embodiment.

In the several embodiments provided in this application, it should be understood that the disclosed system, apparatus, and method may be implemented in other manners. For example, the described apparatus embodiment is merely an example. For example, division into the units is merely logical function division and may be other division in an actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected based on actual requirements to achieve the objectives of the solutions of the embodiments.

In addition, functional units in the embodiments of this application may be integrated into one processing unit, or each of the units may exist alone physically, or two or more units are integrated into one unit.

When the functions are implemented in the form of a software functional unit and sold or used as an independent product, the functions may be stored in a computer-readable storage medium. Based on such an understanding, the technical solutions of this application essentially, or the part contributing to the prior art, or some of the technical solutions may be implemented in a form of a software product. The computer software product is stored in a storage medium, and includes several instructions for indicating a computer device (which may be a personal computer, a server, or a network device) to perform all or some of the steps of the methods described in the embodiments of this application. The storage medium includes any medium that can store program code, such as a USB flash drive, a removable hard disk, a read-only memory (ROM), a random access memory (RAM), a magnetic disk, or an optical disc.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. An image processing method, comprising:
obtaining a plurality of image blocks by segmenting a to-be-analyzed pathological image;

inputting the plurality of image blocks to a first analysis model to obtain a first analysis result, wherein the first analysis model classifies each of the plurality of image blocks based on a quantity or an area of suspicious lesion components in the image block, the first analysis result indicates that a type of each of the plurality of image blocks is a first type or a second type, the first type indicates that a quantity or an area of the suspicious lesion components in the image block is greater than or equal to a preset threshold, and the second type indicates that the quantity or the area of the suspicious lesion components in the image block is less than the preset threshold;

inputting at least one image block of the second-type in the first analysis result to a second analysis model to obtain a second analysis result, wherein the second analysis model analyzes a location of a suspicious lesion component of each input image block of the second-type; and obtaining a final analysis result of the pathological image based on the first analysis result and the second analysis result.

2. The image processing method according to claim 1, further comprising:

inputting each of the plurality of image blocks to a third analysis model to obtain a third analysis result, wherein the third analysis model predicts image quality of each of the plurality of image blocks; and the obtaining of the final analysis result of the pathological image based on the first analysis result and the second analysis result comprises:

obtaining the final analysis result of the pathological image based on the first analysis result, the second analysis result, and the third analysis result.

3. The image processing method according to claim 1, wherein the obtaining of the plurality of image blocks comprises:

obtaining a plurality of initial image blocks formed after the to-be-analyzed pathological image is segmented; and inputting each of the plurality of initial image blocks to a style transfer model to obtain the plurality of image blocks, wherein the style transfer model converts a style of each of the plurality of initial image blocks.

4. The image processing method according to claim 1, further comprising:

training an initial first analysis model based on a first training data set to obtain the first analysis model, wherein the initial first analysis model is one of artificial intelligence (AI) models, the first training data set comprises a plurality of first training images, and a label of each of the plurality of first training images is a first type or a second type.

5. The image processing method according to claim 1, further comprising:

training an initial second analysis model based on a second training data set to obtain the second analysis model, wherein the initial second analysis model is one of artificial intelligence (AI) models, the second training data set comprises a plurality of second training images comprising a suspicious lesion component, and a label of each of the plurality of second training images is location information of the suspicious lesion component in the second training image.

6. The image processing method according to claim 1, further comprising:

training an initial third analysis model based on a third training data set to obtain the third analysis model, wherein the initial third analysis model is one of artificial intelligence (AI) models, the third training data set comprises a plurality of third training images, and a label of each of the plurality of third training images is an image quality type of the third training image.

7. The image processing method according to claim 1, wherein the obtaining of the final analysis result of the pathological image based on the first analysis result and the second analysis result comprises:

inputting the first analysis result and the second analysis result to a decision model to obtain the final analysis result of the pathological image.

8. A computing device including a memory and at least one processor, the memory stores computer instructions that, when executed by the at least one processor, cause the computing device to:

obtain a plurality of image blocks by segmenting a to-be-analyzed pathological image;

input the plurality of image blocks to a first analysis model to obtain a first analysis result, wherein the first analysis model classifies each of the plurality of image blocks based on a quantity or an area of suspicious lesion components in the image block, the first analysis result indicates that a type of each of the plurality of image blocks is a first type or a second type, the first type indicates that a quantity or an area of the suspicious lesion components in the image block is greater than or equal to a preset threshold, and the second type indicates that the quantity or the area of the suspicious lesion components in the image block is less than the preset threshold; and input at least one image block of the second-type in the first analysis result to a second analysis model to obtain a second analysis result, and the second analysis model analyzes a location of a suspicious lesion component of each input image block of the second-type; and obtain a final analysis result of the pathological image based on the first analysis result and the second analysis result.

9. The computing device according to claim 8, wherein the memory further stores computer instructions that, when executed by the at least one processor, cause the computing device to:

input each of the plurality of image blocks to a third analysis model to obtain a third analysis result, the third analysis model predicts image quality of each of the plurality of image blocks, and obtain the final analysis result of the pathological image based on the first analysis result, the second analysis result, and the third analysis result.

10. The computing device according to claim 8, wherein the memory further stores computer instructions that, when executed by the at least one processor, cause the computing device to:

obtain a plurality of initial image blocks formed after the to-be-analyzed pathological image is segmented, and input each of the plurality of initial image blocks to a style transfer model to obtain the plurality of image blocks, and the style transfer model converts a style of each of the plurality of initial image blocks.

11. The computing device according to claim 8, wherein the memory further stores computer instructions that, when executed by the at least one processor, cause the computing device to:

train an initial first analysis model based on a first training data set to obtain the first analysis model, the initial first analysis model is one of artificial intelligence (AI) models, the first training data set comprises a plurality of first training images, and a label of each of the plurality of first training images is a first type or a second type.

12. The computing device according to claim 8, wherein the memory further stores computer instructions that, when executed by the at least one processor, cause the computing device to:
train an initial second analysis model based on a second training data set to obtain the second analysis model, the initial second analysis model is one of artificial intelligence (AI) models, the second training data set comprises a plurality of second training images comprising a suspicious lesion component, and a label of each of the plurality of second training images is location information of the suspicious lesion component in the second training image.

13. The computing device according to claim 8, wherein the memory further stores computer instructions that, when executed by the at least one processor, cause the computing device to:
train an initial third analysis model based on a third training data set to obtain the third analysis model, the initial third analysis model is one of artificial intelligence (AI) models, the third training data set comprises a plurality of third training images, and a label of each of the plurality of third training images is an image quality type of the third training image.

14. The computing device according to claim 8, wherein the memory further stores computer instructions that, when executed by the at least one processor, cause the computing device to:
input the first analysis result and the second analysis result to a decision model to obtain the final analysis result of the pathological image.

15. A non-transitory computer readable storage medium, storing computer program code that, when executed by a computing device, causes the computing device to:
obtain a plurality of image blocks by segmenting a to-be-analyzed pathological image;
input the plurality of image blocks to a first analysis model to obtain a first analysis result, wherein the first analysis model classifies each of the plurality of image blocks based on a quantity or an area of suspicious lesion components in the image block, the first analysis result indicates that a type of each of the plurality of image blocks is a first type or a second type, the first type indicates that a quantity or an area of the suspicious lesion components in the image block is greater than or equal to a preset threshold, and the second type indicates that the quantity or the area of the suspicious lesion components in the image block is less than the preset threshold; and
input at least one image block of the second-type in the first analysis result to a second analysis model to obtain a second analysis result, and the second analysis model analyzes a location of a suspicious lesion component of each input image block of the second-type; and
obtain a final analysis result of the pathological image based on the first analysis result and the second analysis result.

16. The non-transitory computer readable storage medium according to claim 15, wherein, when executed by the computing device, the computer program code further causes the computing device to:
input each of the plurality of image blocks to a third analysis model to obtain a third analysis result, the third analysis model predicts image quality of each of the plurality of image blocks, and
obtain the final analysis result of the pathological image based on the first analysis result, the second analysis result, and the third analysis result.

17. The non-transitory computer readable storage medium according to claim 15, wherein, when executed by the computing device, the computer program code further causes the computing device to:
obtain a plurality of initial image blocks formed after the to-be-analyzed pathological image is segmented, and input each of the plurality of initial image blocks to a style transfer model to obtain the plurality of image blocks, and the style transfer model converts a style of each of the plurality of initial image blocks.

18. The non-transitory computer readable storage medium according to claim 15, wherein, when executed by the computing device, the computer program code further causes the computing device to:
train an initial first analysis model based on a first training data set to obtain the first analysis model, the initial first analysis model is one of artificial intelligence (AI) models, the first training data set comprises a plurality of first training images, and a label of each of the plurality of first training images is a first type or a second type.

19. The non-transitory computer readable storage medium according to claim 15, wherein, when executed by the computing device, the computer program code further causes the computing device to:
train an initial second analysis model based on a second training data set to obtain the second analysis model, the initial second analysis model is one of artificial intelligence (AI) models, the second training data set comprises a plurality of second training images comprising a suspicious lesion component, and a label of each of the plurality of second training images is location information of the suspicious lesion component in the second training image.

20. The non-transitory computer readable storage medium according to claim 15, wherein, when executed by the computing device, the computer program code causes the computing device to:
train an initial third analysis model based on a third training data set to obtain the third analysis model, the initial third analysis model is one of artificial intelligence (AI) models, the third training data set comprises a plurality of third training images, and a label of each of the plurality of third training images is an image quality type of the third training image.

* * * * *